United States Patent [19]

Eggensperger et al.

[11] 4,259,383

[45] Mar. 31, 1981

[54] DISINFECTING TISSUE

[75] Inventors: Heinz Eggensperger, Hamburg; Dieter Rehn, Norderstedt; Wolfgang Beilfuss, Hamburg-Hummelsbüttel; Helmut Nolte, Tangstedt, all of Fed. Rep. of Germany

[73] Assignee: Sterling Drug Inc., New York, N.Y.

[21] Appl. No.: 52,264

[22] Filed: Jun. 26, 1979

[30] Foreign Application Priority Data

Jun. 30, 1978 [DE] Fed. Rep. of Germany ....... 2828724

[51] Int. Cl.³ .......................... B32B 3/02; B32B 3/12
[52] U.S. Cl. ....................................... 428/72; 422/28; 422/29; 422/37; 428/76; 428/166; 428/194
[58] Field of Search ............... 422/28, 29, 37; 424/27, 424/28, 29; 128/113, 114; 428/68, 76, 166, 72, 178, 194, 240, 283, 907

[56] References Cited

U.S. PATENT DOCUMENTS

| 1,955,891 | 4/1934 | Salzberg et al. | 428/907 |
| 2,381,852 | 8/1945 | Hochwalt | 428/907 |
| 2,709,665 | 5/1955 | Campbell et al. | 428/906 |
| 3,490,454 | 1/1970 | Goldfarb et al. | 428/907 |
| 3,594,468 | 7/1971 | Saurino et al. | 424/28 |
| 3,817,702 | 6/1974 | Paulus et al. | 428/907 |
| 3,964,486 | 6/1976 | Blaney | 424/28 |
| 4,029,758 | 6/1977 | Mlodozeniec et al. | 424/27 |

OTHER PUBLICATIONS

The Merck Index, (9th Ed.), Pub. by Merck & Co. Inc., (1976), pp. 1118, 1119, 142, 143.

Primary Examiner—William J. Van Balen
Attorney, Agent, or Firm—Frederik W. Stonner; B. Woodrow Wyatt

[57] ABSTRACT

A disinfecting tissue comprising an absorbent material having incorporated therein a disinfecting agent selected from (a) organic percarboxylic acids; (b) mixtures of a hydrogen peroxide donor with an organic carboxylic acid anhydride or a acyloxy-benzoic or -benzenesulfonic acid; and (c) a carboxylic acid amide; as defined in the specification. The disinfectant tissues are useful for the disinfection of the skin, hands, and inanimate surfaces.

5 Claims, 5 Drawing Figures

DISINFECTING TISSUE

BACKGROUND OF THE INVENTION

1. Field of the Invention

The invention relates to disinfecting tissues useful for disinfecting the skin, for example, for the pre-operative preparation of patients and disinfection of surgeons' hands, and inanimate surfaces.

2. Description of the Prior Art

The disinfecting agents customarily employed in skin and hand disinfection are mainly aldehyde- or phenol-based mixtures or suitable detergents or soaps containing such mixtures as well as peracetic acid solutions. The disadvantage of these agents resides in the known toxic effects such as allergies, skin irritation by alcohol or soap, and corrosiveness of the peracetic acid, which effects severely limit the application of such preparations. Also, in the case of surface disinfection, the indicated agents are not optimal. Aside from dosage problems, annoying odors and allergic manifestations, the problem of corrosiveness with respect to various materials has not yet been solved satisfactorily.

Dispensers for absorbent sheeting in the form of a coreless roll placed in a container, where the absorbent material is impregnated with alcohol or other liquids and can be pulled from the container through an aperture are known, for example, U.S. Pat. No. 4,017,002. Such containers, however, are relatively bulky and have the disadvantage that the impregnating or disinfecting agents not only are readily volatilized but also exhibit the hereinabove described disadvantages of the known disinfectants.

Tissues which deliver other agents are known, such as, for example, menthol-impregnated paper handkerchiefs or silver polishing cloths impregnated with polishing agent, where the agent is distributed across the whole fiber matrix of the sheeting. Such tissues, intended for single or multiple applications, have the disadvantage that the active agent can emerge from the sheeting or liberate dust, so that exterior packing is necessary to prevent loss of the active agent from the merchandise upon storage. Cloth-like sheeting that is soaked with liquid agents, and sponge-like structures into which a plastic ampule with liquid is incorporated are known. The liquid soaked cloths have the disadvantage that they must be covered with an impermeable membrane, such as plastic, in order to prevent premature evaporation of the liquid agent. Considerable effort is required to break the ampules incorporated into the sponge-like structures, in order to liberate the active liquid for use.

OBJECT OF THE INVENTION

It is an object of this invention to provide toxicologically unobjectionable disinfecting agents, useful for skin, hand, and surface disinfection, in the form of tissues having disinfectants incorporated therein, which can be manufactured in a simple manner, which can be stored without undue precautions, which are immediately usable and which, when containing a dry disinfectant, are converted into their disinfectant forms upon moistening with water.

SUMMARY OF THE INVENTION

This invention provides a disinfecting tissue comprising an absorbent material having incorporated therein a disinfecting agent where the disinfecting agent is selected from the group consisting of:

(a) an organic percarboxylic acid of the formula

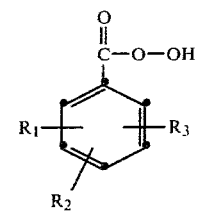

where $R_1$, $R_2$ and $R_3$ independently are hydrogen, chlorine, bromine, fluorine, nitro, cyano, trifluoromethyl, carboxy, methoxycarbonyl, aminocarbonyl, straight or branched alkyl having from 1 to 5 carbon atoms, phenyl, methoxy, ethoxy, acetyloxy, acetyl or hydroxysulfonyl, provided that at least one of $R_1$, $R_2$ and $R_3$ is not hydrogen, or $R_2$ and $R_3$, when attached to adjacent ring carbon atoms, form together with the adjacent ring carbon atoms an aromatic ring;

(b) a mixture comprising an agent capable of generating hydrogen peroxide in water; and a compound selected from the group consisting of an organic carboxylic acid anhydride, and an acyloxy acid of the formula

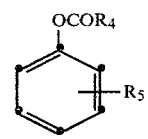

where $R_4$ is lower-alkyl which is unsubstituted or substituted by a substituent selected from the group consisting of hydroxy, lower-alkoxy, lower-alkanoyloxy, carboxy and halo; or $R_4$ is phenyl which is unsubstituted or substituted by a substituent selected from the group consisting of lower-alkyl, lower-alkoxy, hydroxy and halo; and $R_5$ is carboxy or hydroxysulfonyl, and water-soluble salts of the acyloxy-acid; and (c) a carboxylic acid amide of the formula

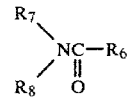

where $R_6$, $R_7$ and $R_8$ independently are hydrogen, lower-alkyl, cycloalkyl, aryl or aryl-lower-alkyl, or $R_6$ and $R_7$ together with the carbonyl and nitrogen respectively to which they are attached form a lactam having from 4 to 8 ring atoms; and mixtures of two or all three of (a), (b) and (c).

In one preferred aspect of the invention the disinfecting tissue is comprised of two layers of the absorbent material which are joined at their margins, the disinfecting agent being disposed between the two layers.

In another preferred aspect of the invention the disinfecting tissue is comprised of two layers of the absorbent material which are joined to form a multiplicity of pockets, the disinfecting agent being disposed in the pockets.

In yet another preferred aspect of the invention, the disinfecting tissue has the disinfecting agent physically incorporated therein by impregnation; or by matting of the agent in granular or powder form with the fibers of the absorbent material.

In yet another preferred aspect of the invention, the disinfecting agent incorporated in the disinfecting tissue comprises a mixture of an agent capable of generating hydrogen peroxide in water and an organic carboxylic acid anhydride, more preferably, where the carboxylic acid anhydride is selected from the group consisting of succinic anhydride, maleic anhydride, glutaric anhydride, phthalic anhydride, itaconic anhydride, homophthalic anhydride, 1,2,4,5-benzene-tetracarboxylic acid anhydride, 1,2,4-benzene-tricarboxylic acid anhydride, 1,2,3-benzene-tricarboxylic acid anhydride, benzoylcitric acid anhydride, dibenzoyltartaric acid anhydride and benzoic anhydride.

DETAILED DESCRIPTION INCLUSIVE OF THE PREFERRED EMBODIMENTS

Figure 1:
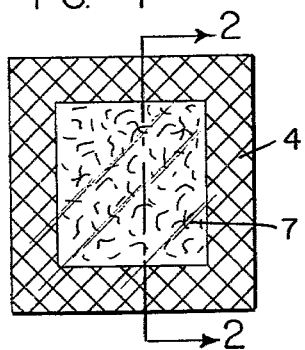
FIG. 1 represents a top view of one embodiment of the tissue in accordance with the invention.

The absorbent material can be formed of natural, synthetic or mixed textile materials, of textile or cellulose fiber fleece, or of suitable paper. The size and form of the tissues depend on the intended end use. The absorbent material can be in the form of a single tissue or of a web or ribbon which is severable into individual tissues. The web or ribbon can be rolled or folded. The tissues can be packaged singly or, in larger containers, preferably are provided as a web which is in roll form, severable into individual sheets, e.g. by means of perforations at regular intervals. The absorbent material should be porous and water-permeable; and when the disinfecting agent is positioned between layers thereof, it is preferably a tangled fiber fleece on a cellulose or polymer base, as for example a polypropylene tangled fiber fleece. The effective pore size of the sheeting should be smaller than the particle size of the disinfecting agent. By effective pore size is meant the available aperture perpendicular to the material layer which separates the disinfecting agent from the outer atmosphere. For example, the effective pore size in a tangled fiber fleece is considerably smaller than the pore size of the tangled fiber fleece on the surface of the sheeting. The pore size should be of the order of magnitude of a few $\mu$ to 150$\mu$.

In the tissue of the invention, the disinfecting agent can be conveniently disposed in one or several cavities or pockets between at least 2 layers of the absorbent material, the pockets containing the disinfectant being sealed in a manner that prevents the disinfecting agent from emerging from the margin of the tissue. Preferably, if several cavities or pockets are provided in the tissue for receiving the disinfecting agent, the individual pockets are essentially sealed one from the other.

The sealing of the marginal areas of the tissue and individual pockets can be carried out with pressure, for example, by lamination or pressure sealing, or alternatively by glueing them together. For example, the sealing can be carried out by means of a heat sealable plastic.

The manufacture of the tissues of the invention can be carried out in a simple manner utilizing conventional techniques and equipment. For example, the disinfecting agent can be applied in portions on one sheet of absorbent material which then is covered with a cover layer or a second layer of the absorbent material, the two sheets subsequently being sealed at their margins. This can be carried out by passing the layered structure with the disinfecting agent disposed therein through calender rollers which effect the sealing of the two sheets of absorbent material. The sheeting can subsequently be divided into smaller segments, i.e., tissues, provided, however, that the pockets containing the disinfecting agent remain intact by this separation. It is also possible to employ sheeting onto which before, during or after addition of the disinfecting agent, a plastic adhesive strip is applied, heat-sealable polyethylene adhesives being particularly suitable for this purpose. The sheeting, after application of the second layer then is passed through a calender roller, with mild heat application, which presses and thereby seals the adhesive strips.

Disinfectants which can be employed in the invention and which are changed into their disinfecting forms on moistening with water are the organic percarboxylic acid of formula I hereinabove. Examples of such acids are: 4-cyanoperbenzoic acid, 4-tert-butylperbenzoic acid, 3-tert-butylperbenzoic acid, 2-tert-butylperbenzoic acid, 4-nitroperbenzoic acid, 4-fluoroperbenzoic acid, 3-chloroperbenzoic acid, 2,4-dichloroperbenzoic acid, 4-chloroperbenzoic acid, 4-methoxyperbenzoic acid, 2-methylperbenzoic acid, 3-methylperbenzoic acid, 4-methylperbenzoic acid, 3,4,5-trimethoxyperbenzoic acid, monoperphthalic acid and 1-pernaphthoic acid. Particularly preferred are 4-tert-butylperbenzoic acid, 3-chloroperbenzoic acid, 4-methylperbenzoic acid and 4-methoxyperbenzoic acid.

Other disinfecting agents which can be employed and which are changed into their disinfecting form on moistening with water are mixtures of the acyloxy acids of formula II hereinabove with agents capable of generating hydrogen peroxide in water, i.e., $H_2O_2$ donors, for example, salts of inorganic peracids.

Examples of preferred acyloxy acids are the following O-acyl compounds: acetyl-, propionyl-, benzoyl-, (4-methoxybenzoyl)-, (3-chlorobenzoyl)-, (4-tert-butylbenzoyl)- and (4-methylbenzoyl)-salicylic acid; 3-acetoxy-, 3-propionyloxy-, 3-benzoyloxy-, 3-(4-methoxybenzoyloxy)-, 3-(3-chlorobenzoyloxy)-, 3-(4-tert-butylbenzoyloxy)- and 3-(4-methylbenzoyloxy)-benzoic acid; and 4-acetoxy-, 4-propionyloxy-, 4-benzoyloxy-, 4-(4-methoxybenzoyloxy)-, 4-(3-chlorobenzoyloxy)-, 4-(4-tert-butylbenzoyloxy)- and 4-(4-methylbenzoyloxy)-benzoic acid. Particularly preferred are acetyl-, benzoyl-, (4-methoxybenzoyl)-, and (4-tert-benzoyl)-salicylic acid; 3-acetoxy-, 3-benzoyloxy- and 3-(4-methoxybenzoyl)-benzoic acid; and 4-acetoxy-, 4-propionyloxy-, 4-benzoyloxy- and 4-(4-methoxybenzoyloxy)-benzoic acid.

It will be understood that the water-soluble salt forms of the acyloxy acids of formula II are, for the purpose of the invention, the full equivalents of the acyloxy acids of formula II. Examples of such salts are the salts of alkali metals, e.g., sodium and potassium, salts of alkaline-earth metals, e.g., calcium and barium, ammonium salts such as those derived from ammonia or mono-, di- and tri-alkylamines, e.g., methylamine, ethylamine, isopropylamine, hexylamine, dimethylamine, methylethylamine, dihexylamine, triethylamine and the like, as well as tetraalkyl ammonium salts, such as the tetramethylammonium salt, tetraethylammonium salt and the like.

As salts of inorganic peracids there can be employed the alkali metal, for example, lithium, sodium and potassium, and ammonium salts of inorganic peracids, for example, alkali metal and ammonium perborate, percarbonate, perphosphate, peroxide, alkali metal and ammonium salts of peroxidisulfuric acid and percarbamic acid.

Mixtures of organic carboxylic acid anhydrides with salts of inorganic peracids, described hereinabove, also can be employed as disinfectants. Such anhydrides can be simple carboxylic acid anhydrides or mixed carboxylic acid anhydrides. Furthermore, the anhydride structure in a molecule can occur once, twice or n-times where n is between 3 and 100. Examples of carboxylic anhydrides which can be employed in the invention are, for example, succinic anhydride, maleic anhydride, glutaric anhydride, phthalic anhydride, itaconic anhydride, benzoic anhydride, diglycolic anhydride, acetylcitric acid anhydride, dichloromaleic anhydride, 3,3-dimethylglutaric anhydride, 2,3-dimethylmaleic anhydride, 2-dodecen-1-ylsuccinic anhydride, homophthalic anhydride, 3-methylglutaric anhydride, 2-phenylglutaric anhydride, tetramethyleneglutaric anhydride, trimethylacetic anhydride, 1,2,4,5-benzenetetracarboxylic acid anhydride, 1,2,4-benzenetricarboxylic acid anhydride, 1,2,3-benzenetricarboxylic acid anhydride, 3,3′,4,4′-benzophenonetetracarboxylic acid dianhydride, 1,4,5,8-naphthalenetetracarboxylic acid dianhydride, 1,8-naphthalene dicarboxylic acid anhydride, 3-nitrophthalic anhydride, 3,4,9,10-perylenetetracarboxylic acid dianhydride, tetrabromophthalic acid anhydride, tetrachlorophthalic acid anhydride, tetraphenylphthalic acid anhydride, bicyclo[2.2.2]oct-7-ene-2,3,5,6-tetracarboxylic acid dianhydride, camphoric acid anhydride, cis,cis,cis,cis-1,2,3,4-cyclopentanetetracarboxylic acid dianhydride, cis-4-cyclohexene-1,2-dicarboxylic acid anhydride, tetrahydrofurane-2,3,4,5-tetracarboxylic acid dianhydride, benzoylcitric acid anhydride and dibenzoyltartaric acid anhydride. Particularly preferred are succinic anhydride, maleic anhydride, glutaric anhydride, phthalic anhydride, itaconic anhydride, homophthalic anhydride, 1,2,4,5-benzenetetracarboxylic acid anhydride, 1,2,4- and 1,2,3-benzene-tricarboxylic anhydride, as well as benzoylcitric acid anhydride, dibenzoyltartaric acid anhydride and benzoic anhydride.

Furthermore, the carboxylic acid amides of formula III hereinabove can be employed as disinfectants. Preferred compounds of formula III are formamide, acetamide, propionamide and benzamide.

In addition, the acyloxy acid (formula II) and carboxylic acid amide (formula III) can be chemically bound to the absorbent material in which case the absorbent material is based on carbohydrate and acid amide functions.

The dry disinfectant agent can be physically incorporated in the tissue in several ways. For example, it can be incorporated by impregnation, by matting of the powdered or granular form of the disinfectant agent with the fibers of the absorbent material, or, as indicated hereinabove, by chemical bonding, e.g., by acylation of the absorbent material with the acid chloride derivatives of the compounds of formula II or with the appropriate carboxylic acid anhydride.

As used herein, the terms lower-alkyl, lower-alkoxy, and lower-alkanoyl mean such groups preferably containing from one to six carbon atoms which can be arranged as straight or branched chains, and, without limiting the generality of the foregoing, are illustrated by methyl, ethyl, propyl, isopropyl, butyl, sec-butyl, amyl, hexyl and the like for alkyl; methoxy, ethoxy, propoxy, isobutoxy, hexyloxy and the like for alkoxy; and acetyl, propionyl, butyryl, isobutyryl, hexanoyl and the like for alkanoyl.

As used herein, the term halo means chloro, bromo, iodo and fluoro.

The term cycloalkyl, as used herein, means cycloalkyl radicals having from three to eight ring-carbon atoms and having up to a total of about eight carbon atoms, as illustrated by cyclopropyl, cyclopentyl, cyclohexyl, 2-methylcyclohexyl, 4-ethylcyclohexyl, cyclooctyl, and the like.

The term aryl, as used herein, means such radicals having one to three benzenoid rings as illustrated by phenyl, naphthyl, phenanthrenyl, biphenylyl, and the like.

The term "lactam having from 4 to 8 ring atoms", as used herein, means 2-oxo-trimethyleneimine, 2-oxo-tetramethyleneimine, 2-oxo-pentamethyleneimine, 2-oxo-hexamethyleneimine and 2-oxo-heptamethyleneimine.

In the compounds of formula I, when $R_2$ and $R_3$ together with the adjacent rings to which they are attached form an aromatic ring, the term aromatic ring means such radicals having one to three benzenoid rings as illustrated by benzene, naphthylene, phenanthrene and anthracene. Thus, for example, when $R_2$ and $R_3$ together with adjacent carbon atoms to which they are attached form a benzene ring, formula I represents a 1(or 2)-pernaphthoic acid.

The disinfectant tissue can, if desired, also have incorporated therein a laundry detergent such as soap, anionic, nonionic, ampholytic and/or quaternary surfactants; the laundry additives may also serve as coatings for the active disinfectants. Particularly suitable laundry materials are, for example, fatty acid soaps, alkylbenzenesulfonates, lauryl sulfates, olefinsulfonates, secondary alkylsulfonates, alkylphenyl polyglycol ethers, polyoxypropylene glycols, amine oxides and betaines.

Advantageously, the disinfectant tissue can also have incorporated therein water-binding agents. Suitable water-binding agents are, e.g., calcium chloride, calcium oxide, potassium carbonate, magnesium perchlorate, magnesium sulfate and sodium sulfate.

In addition to the organic peroxides, the acyloxy acids or carboxylic acid amides, respectively, the $H_2O_2$ donors, the coating agents, the water-binding agents and fillers, the tissues can have incorporated therein stabilizers for the peracid and/or $H_2O_2$, pH-adjusting and stabilizing agents, corrosion inhibitors, perfumes, additional antimicrobial substances and dermatologically useful additives.

Suitable stabilizing agents for $H_2O_2$ and/or the peracids are, e.g. urea, alkali salts of metaphosphates, alkali salts of polyphosphates, 2,3-pyridine-dicarboxylic acid, 2,6-pyridine-dicarboxylic acid, citric acid and their alkali salts, ethylenediaminetetraacetic acid and its alkali salts, and nitrilo[tri]acetic acid as well as its alkali salts.

The stabilizers can be present in a concentration of 0.01 to 5%, preferably 0.1 to 5%.

Corrosion inhibitors which can be employed are benzotriazole, alkali phosphate, alkyl phosphate and aminoxide. The corrosion inhibitors can be present in a concentration of to 10%, preferably 0.5 to 5%.

As additional antimicrobial additives, there can be employed, for example, sorbic acid, benzoic acid and salicylic acid.

Agents which can be employed for adjusting and stabilizing the pH value are, for example, citric acid and its salts, alkali phosphates, alkali acetates, lactic acid and its alkali salts, alkali bisulfates, alkali carbonates and alkali bicarbonates.

The pH value of aqueous solutions of the disinfecting tissues of the invention is 3 to 12, preferably 4.5 to 11, and more preferably 6 to 9.

Dermatological skin care additives which can be employed are, e.g., biotin, amino acids, polysaccharides, invert sugar, urea, allantoin and borax.

The invention is illustrated by the following examples without, however, being limited thereto.

The microbiological activity of the below exemplified disinfecting tissues in accordance with the invention was determined by the method for hygienic, or surgical, respectively, hand disinfection in accordance with the Richtlinien für die Prüfung chemischer Disinfektionsmittel der Deutschen Gesellschaft für Hygiene und Mikrobiologie, 3. Aufl., Gustav-Fischer Verlag (DGHM). The disinfecting tissues for surface disinfection were tested in the suspension test and the surface test in accordance with the DGHM.

EXAMPLE 1

A tissue suitable for surface disinfection was prepared from adsorbent non-woven paper (heat-sealing teabag paper) having incorporated therein the following mixture:

|  | % by wt. |
| --- | --- |
| succinic acid anhydride | 40 |
| sodium percarbonate | 45 |
| lauryl sulfate | 7 |
| sodium cumenesulfonate | 3 |
| ethylenediaminetetraacetic acid | 5 |

The microbiological data for these tissues were as follows:

| Suspension test | |
| --- | --- |
| Organism | Killing Time |
| Staphylococcus aureus | 2.5' |
| Pseudomonas aeruginosa | 2.5' |
| Proteus vulgaris | 2.5' |
| Klebsiella pneumoniae | 2.5' |

| Surface test | |
| --- | --- |
| Organism | Killing Time |
| Staphylococcus aureus | 1 h |
| Klebsiella pneumoniae | 1 h |

EXAMPLE 2

A tissue suitable for hand disinfection was prepared from adsorbent non-woven paper (heat-sealing teabag paper) incorporating the following composition:

|  | % by wt. |
| --- | --- |
| benzoic anhydride | 10 |
| sodium polyphosphate | 10 |
| borax | 2.5 |
| sodium percarbonate | 12 |
| allantoin | 0.5 |
| sodium pyrophosphate | 7.5 |
| soap powder | 57.5 |

The test in accordance with the method for hygienic hand disinfection indicated a 70% effectiveness.

The disinfecting tissues of the invention which have disinfectants incorporated on the surface thereof or in some other manner into the tissue, developed antimicrobial efficacy essentially instantaneously and could be utilized readily and practically.

Figure 2:
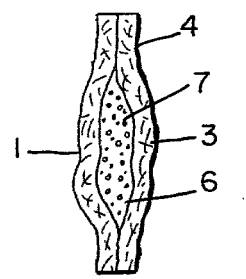
FIG. 2 represents a cross-sectional view taken along the line 2—2 of FIG. 1.

With reference to the drawings, the tissue shown in FIGS. 1 and 2 consists of two layers 1 and 3 of a tangled fiber fleece with a thickness of 0.15 to 0.2 mm and a layer weight of 42 g/m². This tissue has dimensions of ca. 6×6 cm and is pressure sealed at the marginal area 4, so that the two layers 1 and 3 cannot separate from each other. The seal effected at the margin 4 forms a pocket 6 between layers 1 and 3, in which the disinfecting agent 7 is disposed.

Figure 3:
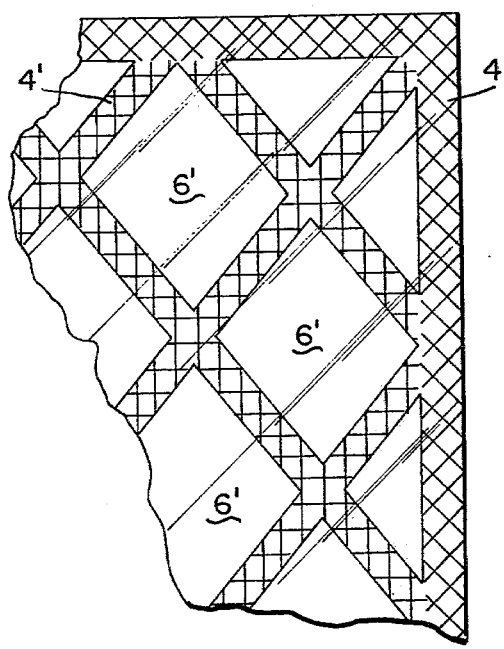
FIG. 3 represents a top view of another embodiment of a tissue in accordance with the invention.

In the embodiment depicted in FIG. 3, the active agent is disposed in several compartments 6' between individual layers. These compartments are formed by a rhomboid stamping 4'. This embodiment has the advantage over the embodiment of FIG. 1, in that the disinfecting agent is more uniformly distributed over the tissue and does not accumulate as a mass at the bottom of the tissue on vertical storage of the tissue as is the case with a tissue having a single pocket.

Figure 4:
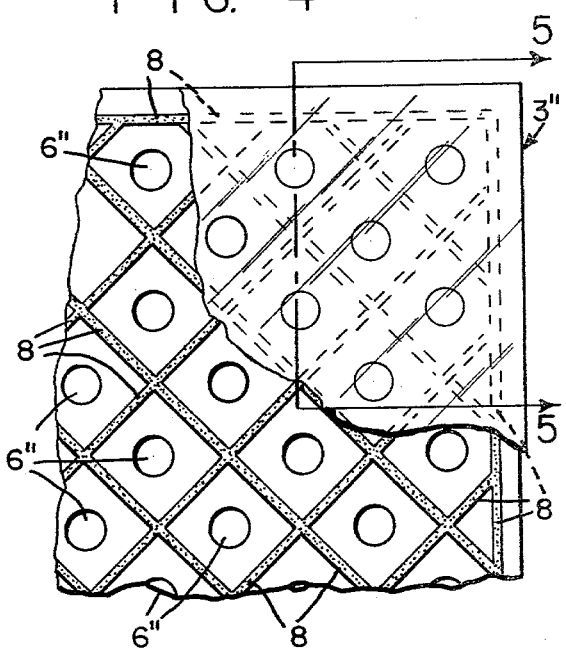
FIG. 4 represents a partial top view of another embodiment of a tissue in accordance with the invention, with the covering layer partially removed.
Figure 5:
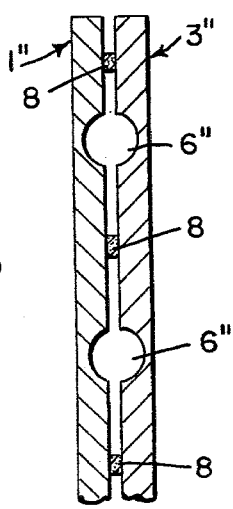
FIG. 5 represents an enlarged cross-sectional view taken along line 5—5 of FIG. 4.

In the embodiment shown in FIGS. 4 and 5, the pockets for receiving the active agent are in the form of small cups 6'' formed, for example, by compressing the sheeting. Between the pockets and at the outer margin are adhesive strips 8, e.g., a heat-sealable polyethylene layer, which upon application of upper cover layer 3'', connects both layers of sheeting 1'' and 3'' after the adhesive has been activated by heating.

We claim:

1. A disinfecting tissue comprising an absorbent material having incorporated therein a disinfecting agent where the disinfecting agent is selected from the group consisting of:

(a) an organic percarboxylic acid of the formula

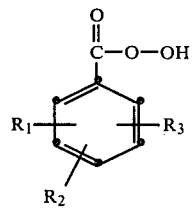

I where $R_1$, $R_2$ and $R_3$ independently are hydrogen, chlorine, bromine, fluorine, nitro, cyano, trifluoromethyl, carboxy, methoxycarbonyl, aminocarbonyl, straight or branched alkyl having from 1 to 5 carbon atoms, phenyl, methoxy, ethoxy, acetyloxy, acetyl or hydroxysulfonyl, provided that at least one of $R_1$, $R_2$ and $R_3$ is not hydrogen, or $R_2$ and $R_3$, when attached to adjacent ring carbon atoms, form together with the adjacent ring carbon atoms an aromatic ring;

(b) a mixture comprising an agent capable of generating hydrogen peroxide in water; and a compound selected from the group consisting of an organic carboxylic acid anhydride, and an acyloxy acid of the formula

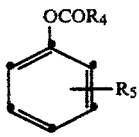   II where $R_4$ is lower-alkyl which is unsubstituted or substituted by a substituent selected from the group consisting of hydroxy, lower-alkoxy, lower-alkanoyloxy, carboxy and halo; or $R_4$ is phenyl which is unsubstituted or substituted by a substituent selected from the group consisting of lower-alkyl, lower-alkoxy, hydroxy and halo; and $R_5$ is carboxy or hydroxysulfonyl, and water-soluble salts of the acyloxy-acid; and (c) a carboxylic acid amide of the formula

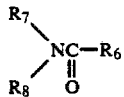   III where $R_6$, $R_7$ and $R_8$ independently are hydrogen, lower-alkyl, cycloalkyl, aryl or aryl-lower-alkyl, or $R_6$ and $R_7$ together with the carbonyl and nitrogen respectively to which they are attached form a lactam having from 4 to 8 ring atoms; and mixtures of two or all three of (a), (b) and (c); wherein the tissue is comprised of two layers of the absorbent material which are joined to form a multiplicity of pockets, the disinfecting agent being disposed in the pockets.

2. A disinfectant tissue in accordance with claim 1 wherein the disinfecting agent comprises a mixture of an agent capable of generating hydrogen peroxide in water and an organic carboxylic acid anhydride.

3. A disinfectant tissue in accordance with claim 2 wherein the agent capable of generating hydrogen peroxide in water is a salt of an inorganic peracid selected from the group consisting of alkali metal perborate, alkali metal percarbonate, alkali metal perphosphate, alkali metal peroxide, alkali metal peroxydisulfate, alkali metal percarbamate, ammonium perborate, ammonium percarbonate, ammonium perphosphate, ammonium peroxide, ammonium peroxydisulfate and ammonium percarbamate.

4. A disinfecting tissue in accordance with claim 3 wherein the carboxylic acid anhydride is selected from the group consisting of succinic anhydride, maleic anhydride, glutaric anhydride, phthalic anhydride, itaconic anhydride, homophthalic anhydride, 1,2,4,5-benzene-tetracarboxylic acid anhydride, 1,2,4-benzene-tricarboxylic acid anhydride, 1,2,3-benzene-tricarboxylic acid anhydride, benzoylcitric acid anhydride, dibenzoyltartaric acid anhydride and benzoic anhydride.

5. A disinfectant tissue in accordance with claim 4 wherein the inorganic peracid is alkali metal percarbonate and the disinfecting agent is succinic anhydride or benzoic anhydride.

* * * * *